(12) United States Patent
Sahabi et al.

(10) Patent No.: US 11,764,745 B2
(45) Date of Patent: Sep. 19, 2023

(54) FILTERED FEEDTHROUGH ASSEMBLY FOR USE IN IMPLANTABLE MEDICAL DEVICE

(71) Applicant: Pacesetter, Inc., Sylmar, CA (US)

(72) Inventors: Kavous Sahabi, Winnetka, CA (US); Jean-Baptiste Fruhauf, Laloubere (FR)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 18/055,253

(22) Filed: Nov. 14, 2022

(65) Prior Publication Data

US 2023/0074562 A1 Mar. 9, 2023

Related U.S. Application Data

(63) Continuation of application No. 16/675,740, filed on Nov. 6, 2019, now Pat. No. 11,528,004.

(60) Provisional application No. 62/757,072, filed on Nov. 7, 2018.

(51) Int. Cl.
| | |
|---|---|
| *H03H 1/00* | (2006.01) |
| *A61N 1/375* | (2006.01) |
| *A61N 1/37* | (2006.01) |
| *H05K 5/02* | (2006.01) |

(52) U.S. Cl.
CPC ............ *H03H 1/00* (2013.01); *A61N 1/3718* (2013.01); *A61N 1/3754* (2013.01); *A61N 1/37512* (2017.08); *H05K 5/0247* (2013.01); *H03H 2001/0014* (2013.01); *H03H 2001/0042* (2013.01)

(58) Field of Classification Search
CPC ............ H03H 1/00; H03H 2001/0042; H03H 2001/0014
USPC .................................................. 333/182, 185
See application file for complete search history.

(56) References Cited

U.S. PATENT DOCUMENTS

| | | |
|---|---|---|
| 4,741,710 A | 5/1988 | Hogan et al. |
| 5,333,095 A | 7/1994 | Stevenson et al. |
| 6,755,779 B2 | 7/2004 | Stevenson et al. |
| (Continued) | | |

FOREIGN PATENT DOCUMENTS

| | | |
|---|---|---|
| EP | 1484085 | 12/2004 |
| EP | 2617461 | 7/2013 |

OTHER PUBLICATIONS

"Thermoplastic Polymide Supported Tape Adhesive", Ableloc 5500 Technical Data Sheet, Oct. 1996 (4 pages).
Integer Letter dated Oct. 24, 2022 (3 pages).

*Primary Examiner* — Rakesh B Patel
(74) *Attorney, Agent, or Firm* — THE SMALL PATENT LAW GROUP LLC; Dean D. Small

(57) ABSTRACT

An implantable pulse generator including a header, a can, and a filtered feedthrough assembly. The header including lead connector blocks. The can coupled to the header and including a wall and an electronic substrate housed within the wall. The filtered feedthrough assembly including a flange mounted to the can and having a feedthrough port, a plurality of feedthrough wires extending through the feedthrough port, and an insulator brazed to the feedthrough port of the flange. The filtered feedthrough assembly further including a capacitor having the plurality of feedthrough wires extending there through, an insulating washer positioned between and abutting the insulator and the capacitor at least in the area of the braze joint such that the capacitor and the braze joint are non-conductive, and an electrically conductive material adhered to the capacitor and the flange for grounding of the capacitor.

20 Claims, 4 Drawing Sheets

(56) References Cited

U.S. PATENT DOCUMENTS

| | | |
|---|---|---|
| 6,888,715 B2 | 5/2005 | Stevenson et al. |
| 7,038,900 B2 | 5/2006 | Stevenson et al. |
| 7,046,499 B1 | 5/2006 | Imani et al. |

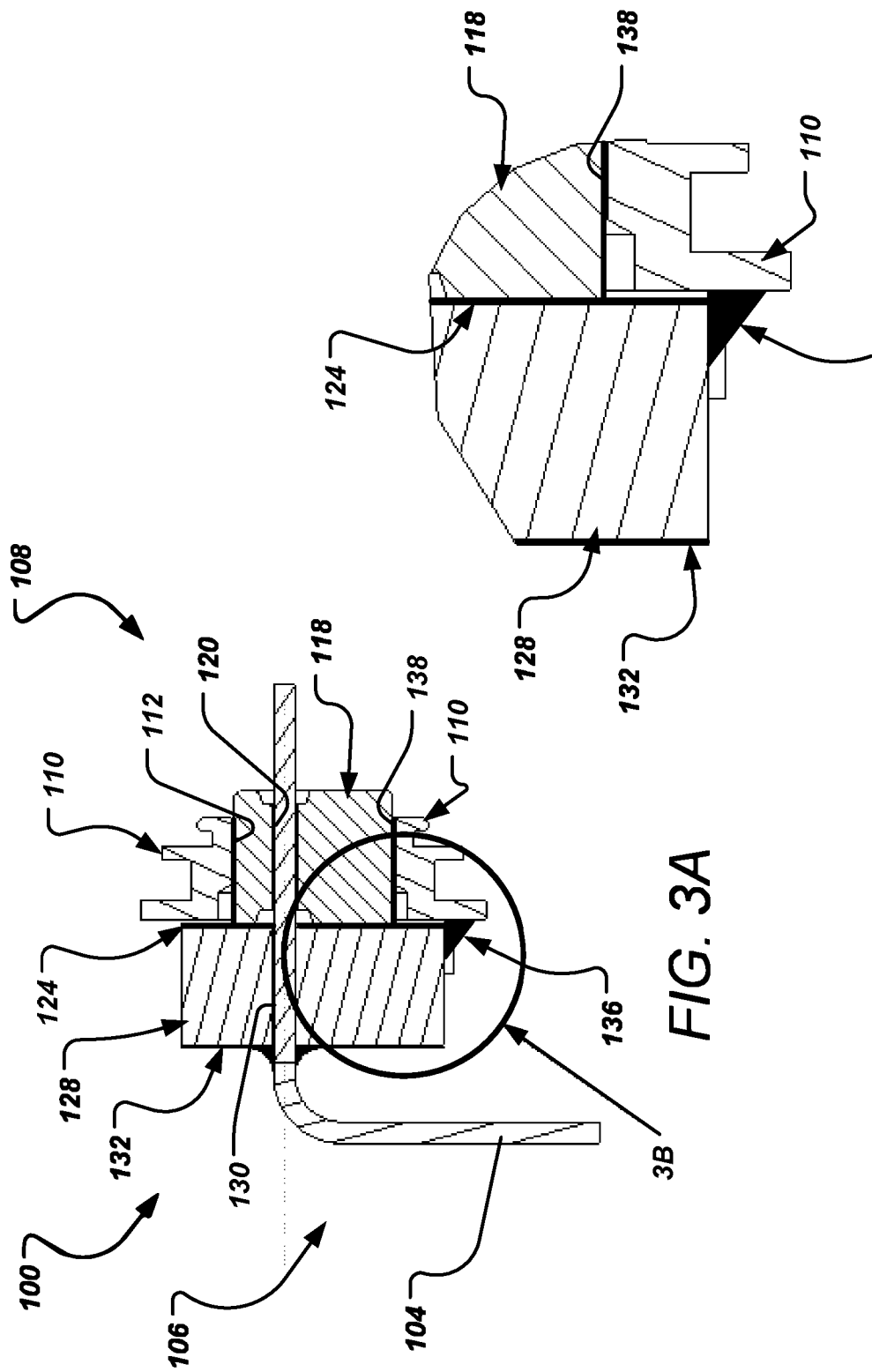

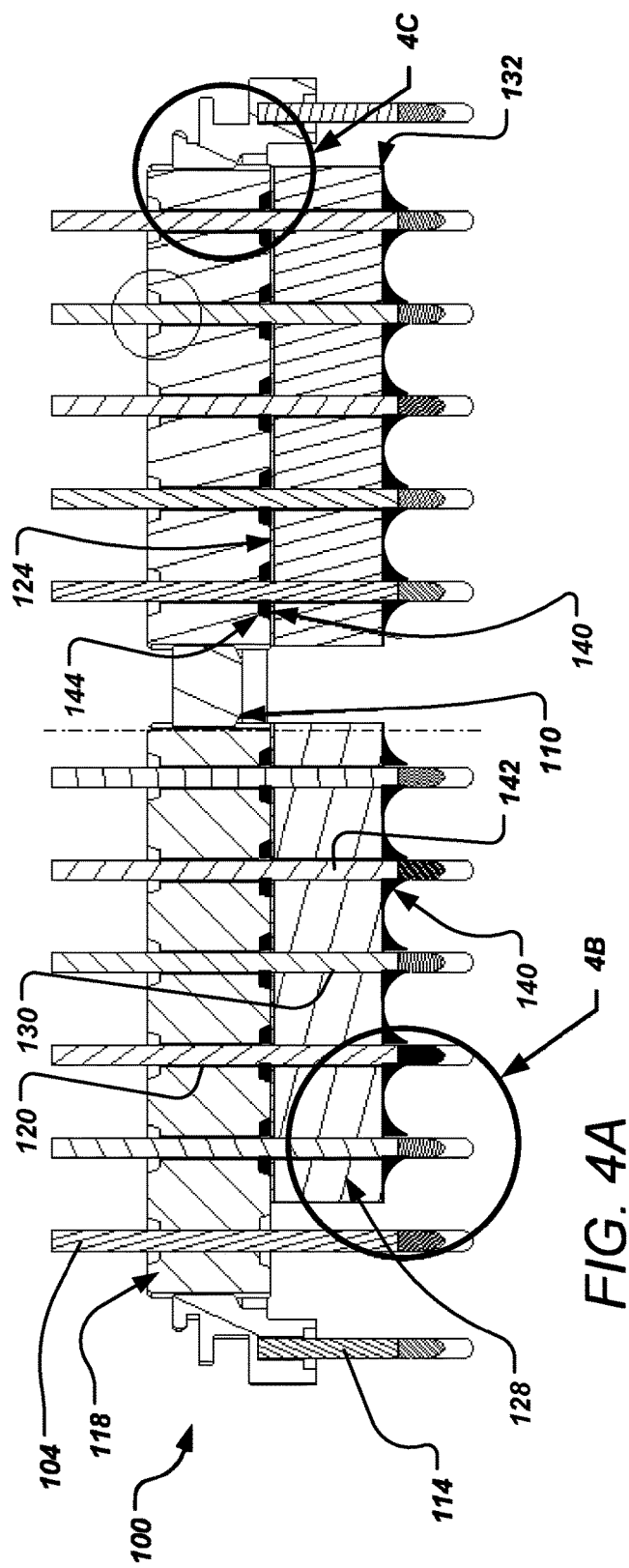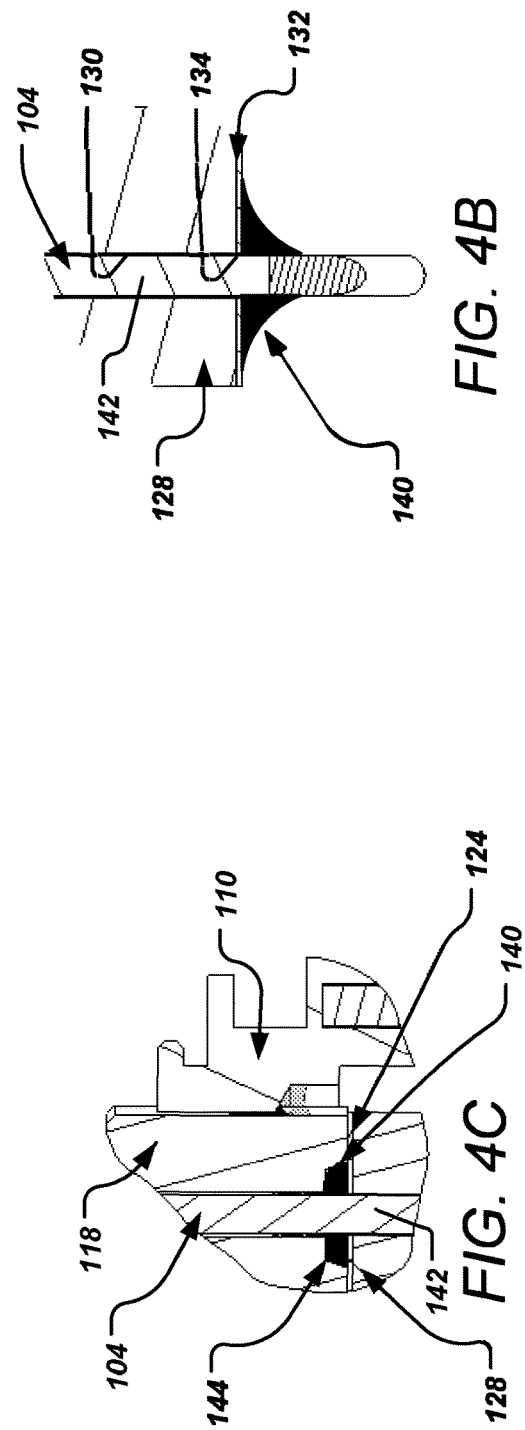

FILTERED FEEDTHROUGH ASSEMBLY FOR USE IN IMPLANTABLE MEDICAL DEVICE

CROSS-REFERENCE TO RELATED APPLICATIONS

This application is a continuation of U.S. Non-Provisional application Ser. No. 16/675,740, filed Nov. 6, 2019, which claims the benefit of U.S. Provisional Application No. 62/757,072, filed Nov. 7, 2018, and both applications are hereby incorporated by reference in their entirety.

FIELD OF THE INVENTION

The present disclosure is directed to feedthrough filter assemblies for use in implantable medical devices such as, for example, cardiac rhythm management and pacemaker devices. More specifically, the present disclosure is directed to the grounding of capacitors in feedthrough filter assemblies.

BACKGROUND OF THE INVENTION

Implantable pulse generators, including cardiovascular implantable electronic devices ("CIED") such as pacemakers and implantable cardioverter defibrillators ("ICD"), are used to provide therapy to cardiac tissue, nerves and other tissue via implantable leads. An implantable pulse generator feedthrough or feedthru is used for an electrical pathway extending between the electrically conductive lead securing components of a header of the pulse generator and the electrical components, such as an output flex, hybrid, etc., hermetically sealed in the housing or can of the pulse generator.

Feedthroughs provide insulated passageways for feedthrough wires, such as platinum iridium (Pt/Ir) wires, through the wall of the can. The header ends of the feedthrough wires are electrically connected to connector blocks that mechanically and electrically couple with proximal connector ends of implantable leads, and the can ends of the feedthrough wires are electrically connected to the electrical components housed in the can of the pulse generator.

Implantable pulse generators may include electromagnetic interference ("EMI") filters for filtering out unwanted EMI signals interfering with the signals from the lead wires. Conventionally, the EMI filter is a capacitor that is sandwiched between the feedthrough and the board. The capacitors are built as monolithic structures that are internally grounded to a flange of the feedthrough assembly. Past attempts at grounding the capacitor to the flange relied on the gold within the braze joint between the insulator and flange to also contact the capacitor and thus provide a conductive path for grounding. This type of grounding can be highly variable depending on the quality of the brazing and the gold mixture within the braze joint. For example, a very thin gold strip between the insulator and the flange may provide excessive resistivity, making the ground unusable in the context of implantable pulse generators. Other problems of relying on the braze material for grounding purposes include the potential for braze failures, for example caused by mechanical strain on the feedthrough assembly and thermal stressing of the braze material.

Accordingly, there is a need in the art for filtered feedthrough assemblies and implantable pulse generators with filtered feedthrough assemblies that are internally grounded that do not rely on grounding through braze material so that improved robustness and reliability of the implantable pulse generator is achieved.

SUMMARY OF THE INVENTION

Aspects of the present disclosure may include a filtered feedthrough assembly for an implantable pulse generator. The filtered feedthrough assembly may include: a flange; a first plurality of feedthrough wires; a first ceramic insulator; an EMI filter; a first non-conductive washer; and a first electrically conductive material. The flange may be formed of an electrically conductive material and may include a can side, a header side, a can side face, header side face, and a first feedthrough port having a first inner surface and extending through the flange from the can side to the header side. The first plurality of feedthrough wires may extend through the first feedthrough port. The first ceramic insulator may include a first outer surface and a first plurality of ports extending there through, the first outer surface of the first ceramic insulator gold brazed to the first inner surface of the first feedthrough port of the flange at a first braze joint, the first plurality of feedthrough wires respectively extending through and gold brazed to the first plurality of ports of the first ceramic insulator. The EMI filter may include a first capacitor having a first plurality of ports extending there through, the first plurality of feedthrough wires respectively extending through the first plurality of ports of the first capacitor. The first non-conductive washer may be positioned between the first ceramic insulator and the first capacitor at the first braze joint such that the first braze joint is non-conducting with the first capacitor. The first electrically conductive material coupling and providing a ground from the first capacitor to the flange.

In certain instances, the first non-conducting washer may include a double-sided adhesive.

In certain instances, the flange further may include a second feedthrough port, and the filtered feedthrough assembly further may include: a second plurality of feedthrough wires; a second ceramic insulator; a second non-conductive washer; and a second electrically conductive material. The second plurality of feedthrough wires may extend through the second feedthrough port. The second ceramic insulator may include a second outer surface and a second plurality of ports extending there through, the second outer surface of the second ceramic insulator gold brazed to a second inner surface of the first feedthrough port of the flange at a second braze joint, the second plurality of feedthrough wires respectively extending through and gold brazed to the second plurality of ports of the second ceramic insulator. The EMI filter further may include a second capacitor having a second plurality of ports extending there through, the second plurality of feedthrough wires respectively extending through the second plurality of ports of the second capacitor. The second non-conductive washer may be positioned between the second ceramic insulator and the second capacitor at the second braze joint such that the second braze joint is non-conducting with the second capacitor. The second electrically conductive material coupling and providing a ground from the second capacitor to the flange.

In certain instances, the feedthrough wires are coated in an electrically conductive adhesive.

In certain instances, the first electrically conductive material includes an electrically conductive adhesive.

In certain instances, the first capacitor is not in direct contact with the flange.

In certain instances, the first capacitor is not in contact with the braze joint.

In certain instances, each of the plurality of ports of the ceramic insulator may include a counter bore, wherein a non-conductive adhesive is adhered to the counter bores.

In certain instances, the filtered feedthrough assembly further may include a first insulating washer coupled to the first capacitor on an opposite side as the first non-conductive washer.

In certain instances, the filtered feedthrough assembly further may include a non-conductive adhesive adhered to the first plurality of feedthrough wires at egress from the first capacitor.

Aspects of the present disclosure may include an implantable pulse generator including: a header; a can; and a filtered feedthrough assembly. The header may include lead connector blocks. The can may be coupled to the header and include a wall and an electronic substrate housed within the wall. The filtered feedthrough assembly may include a flange mounted to the wall of the can and having a feedthrough port, a plurality of feedthrough wires extending through the feedthrough port and electrically connecting the lead connector blocks and the electronic substrate, an insulator brazed to the feedthrough port of the flange at a braze joint and having the plurality of feedthrough wires extending there through, a capacitor having the plurality of feedthrough wires extending there through, an insulating washer positioned between and abutting the insulator and the capacitor at least in the area of the braze joint such that the capacitor and the braze joint are non-conductive, and an electrically conductive material adhered to the capacitor and the flange for grounding of the capacitor.

In certain instances, the insulating washer may include an electrically non-conductive double-sided adhesive.

In certain instances, the electrically conductive material may include an electrically conductive adhesive.

In certain instances, the electrically conductive material couples to a portion of a face of the flange.

In certain instances, the portion of the face of the flange does not surround the feedthrough port of the flange.

In certain instances, the insulator may include feedthrough ports, each of which includes a counter bore, each of the counter bores having a non-conductive adhesive adhered thereto.

In certain instances, the filtered feedthrough assembly further may include an insulating material adhered to the capacitor on a side opposite the insulating washer.

In certain instances, a non-conductive adhesive is adhered to the plurality of feedthrough wires as the plurality of feedthrough wires egress the capacitor.

In certain instances, further may include a ground pin electrically coupled to the flange.

In certain instances, an electrically conductive material is adhered to the plurality of feedthrough wires where they extend through the capacitor.

BRIEF DESCRIPTION OF THE DRAWINGS

FIG. 3A is a side cross-sectional view of the filtered feedthrough assembly.

FIG. 3B is a close-up portion of the filtered feedthrough assembly of FIG. 3A illustrating the conductive adhesive electrically connecting the EMI filter and the flange.

FIG. 4A is a top cross-sectional view of the filtered feedthrough assembly.

FIG. 4B is a close-up portion of the filtered feedthrough assembly of FIG. 4A illustrating the counter bore of the ceramic insulator.

FIG. 4C is a close-up portion of the filtered feedthrough assembly of FIG. 4A illustrating the non-conductive adhesive adhered to the feedthrough wire as it egresses the EMI filter.

DETAILED DESCRIPTION

The present disclosure describes a filtered feedthrough assembly of an implantable pulse generator such as, for example, a pacemaker or an ICD. For a general discussion of an implantable pulse generator 5 that utilizes a feedthrough assembly coupled to a filter (e.g., capacitor) and an inline array feedthrough board, reference is first made to FIG. 1.

Figure 1:
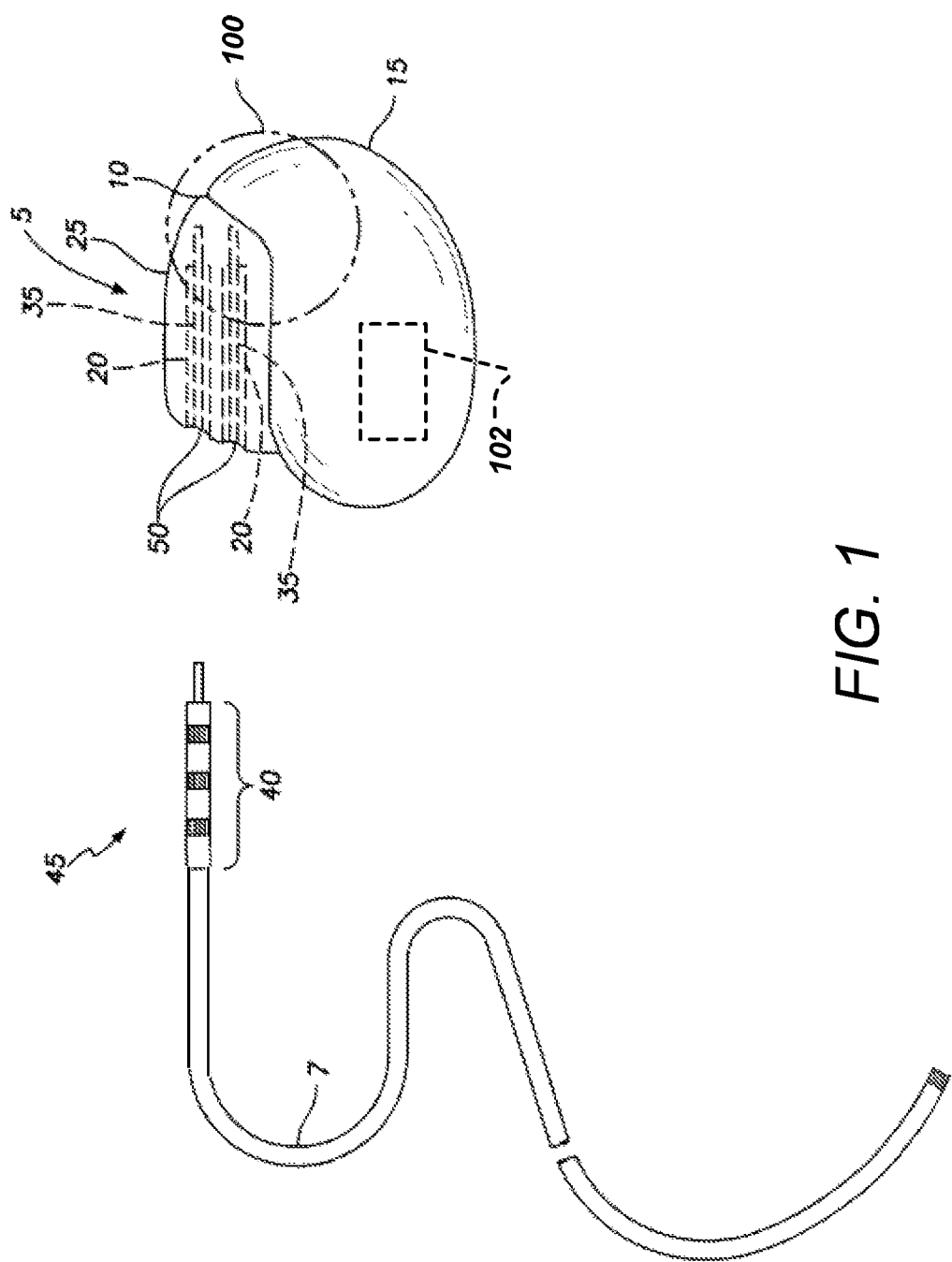
FIG. 1 is a side view of a pulse generator and an implantable lead positioned to be coupled to the pulse generator.

FIG. 1 is a side view of a pulse generator 5 and an implantable lead 7 positioned to be coupled to the pulse generator. As indicated in FIG. 1, the pulse generator 5 includes a header 10 and a can or housing 15. The header 10 includes connector blocks 20 and a molded portion 25 that encloses the connector blocks 20. Each connector block 20 includes an opening 35 configured to receive therein and mate with a connector end 40 of a proximal end 45 of an implantable lead 7, thereby forming an electrical connection between the connector block 20 and the lead connector end 40 and mechanically securing the proximal end 45 of the lead 7 to the header 10 of the pulse generator 5.

The molded header portion 25 may be formed of a polymer material or epoxy. Passages 50 extend from the exterior of the molded portion 25 to the openings 35 in the connector blocks 20 provide a pathway for the lead distal ends 40 to pass through the molded portion 25 and enter the openings 35.

The feedthrough assembly 100, generally located by the broken line circle in FIG. 1, provides an electrical connection between the fixed electrical components 102 within the can 15 and the releasable connection with the connector ends 40 of the proximal end 45 of the lead 7. The can 15 provides a hermetically sealed enclosure for the pulse generator's electronic components (e.g., hybrid, or various other electronic components), which are mounted on, and electrically interconnected via, an electronic substrate, all of which are housed within the can 15. As described previously, the feedthrough assembly 100 may be a filtered feedthrough assembly 100 with the addition of a filtering component, such as an EMI filter. And while an EMI filter is referenced herein, the filtering component may be other types of filters without limitation.

Figure 2:
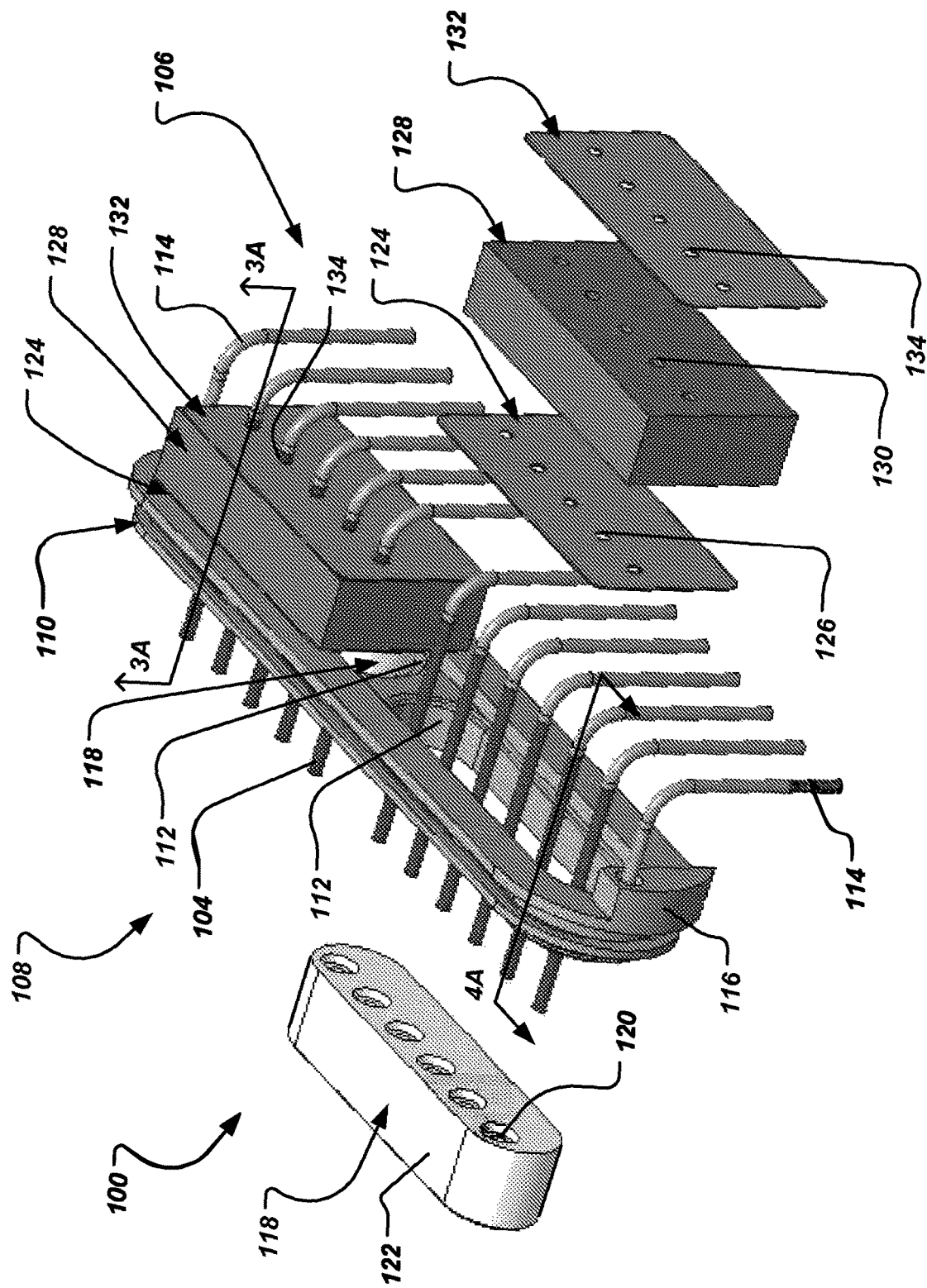
FIG. 2 is an isometric view of a filtered feedthrough assembly, half of which is shown exploded.

To begin the discussion of the filtered feedthrough assembly 100, reference is made to FIG. 2, which depicts an isometric exploded view of half of the filtered feedthrough assembly 100 with the other half in an assembled state. The filtered feedthrough assembly 100 includes feedthrough wires 104 that extend from a can side 106 to a header side 108 of the assembly 100. The feedthrough wires 104 may be made of gold, platinum, nickel, titanium, palladium/iridium, MP35N, or any other suitable material. The filtered feedthrough assembly 100 further includes a flange 110 having an elongated body and a pair of feedthrough ports 112 through which the feedthrough wires 104 extend. The flange 110 may be made of titanium, for example, among other suitable materials. The ports 112 are illustrated as elongated rectangular ports having rounded ends. The ports 112 are of different lengths as one of the ports accommodates six feedthrough wires 104 and the other port 112 accommodates five feedthrough wires 112. As seen in FIG. 2, six feedthrough wires 104 extend through each of the feedthrough ports 112. It should be appreciated that the ports 112 of FIG. 2 are merely examples and that in other implementations, more or fewer ports may be included and/or ports may be provided with different shapes/lengths.

The filtered feedthrough assembly 100 includes two ground pins 114 that may be electrically connected with the internal electronics 102 (not seen in FIG. 2) on the inside of the can 15 (not seen in FIG. 2). As seen in FIG. 2, each of the ground pins 114 may terminate at a projection 116 that juts out from the elongated body of the flange 110. The flange 110 is formed of an electrically conducting material, and therefore provides a conductive path between the ground pins and the can 15 within which the flange 110 is disposed.

The feedthrough wires 104 are isolated from contact with each other and the flange 110 by a pair of ceramic insulators 118 that are sized to fit within the feedthrough ports 112 of the flange 110. The ceramic insulators 118 (generally referred to as insulators) are formed of a non-conducting material and include respective series of wire ports 120 for the feedthrough wires 104 to extend through. The ceramic insulators 118 include an outer surface 122 sized just smaller than the feedthrough ports 112. In this instance, there are two ceramic insulators 118 of different sizes. One of the ceramic insulators 118 includes six wire ports 120 to accommodate the six feedthrough wires 104. And the other ceramic insulator 118 includes five wire ports 120 to accommodate the five feedthrough wires 104. Thus, the two ceramic insulators 118 accommodate a total of eleven feedthrough wires 104. Other arrangements of insulators, including other quantities of insulators and/or insulators accommodating different quantities of feedthrough wires may be used in other implementations of the present disclosure.

The outer surfaces 122 of the ceramic insulators 118 are brazed to the inner surface of the feedthrough ports 112 of the flange 110 at a braze joint using gold, nickel, platinum, or other suitable material as the braze material. As an alternative to brazing, the ceramic insulators 118 may be coupled to the flange via soldering, welding, or other suitable methods. The feedthrough wires 104 may also be connected to the ports 120 of the ceramic insulators 118 via gold brazing. Alternatives may include soldering, welding, or other suitable methods. These methods help ensure a hermetic seal through the filtered feedthrough assembly 100.

On the can side 106 of the filtered feedthrough assembly 100, a double-sided insulating adhesive washer or tape 124 may be attached to the face of the ceramic insulators 118 and the face of the flange 110. The double-sided adhesive washer 124 is non-conducting and includes wire ports 126 for the passage of the feedthrough wires 104. The filtered feedthrough assembly 100 includes an EMI filter 128 in the form of a capacitor that is attached to the other side of the double-sided adhesive washer 124. The EMI filter 128 includes wire ports 130 (also known as via holes) for the feedthrough wires 104 to extend through. The feedthrough wires 104 are attached to the EMI filter 128 using electrically conductive adhesive in the wire ports 130. On the opposite side of the EMI filter 128 is attached an insulating washer 132 having wire ports 134 for the feedthrough wires 104 to extend through.

The EMI filters 128 shunt electromagnetic interference and redirect noise associated with such interference to ground. As described, the EMI filters 128 are insulated from contact with the flange 110 and the braze joint (between the outer surface 122 of the insulator 118 and the feedthrough ports 112) by the double-sided insulating washer 124. Grounding of the EMI filter 128 is accomplished by a conductive adhesive 136 that is applied to the EMI filter 128 and the flange 110 along a length of the lower face of the flange 110 on the can side 106, as seen in FIGS. 3A and 3B. FIG. 3A depicts a side cross-sectional view of the filtered feedthrough assembly 100 through the cross-section line 3A on FIG. 2. The cross-section is taken through one of the feedthrough wires 104. As seen in FIG. 3A, the double-sided insulating washer 124 separates the EMI filter 128 from contact with the ceramic insulator 118 and the flange 110. At a bottom of the EMI filter 128, on the can side 106, the conductive adhesive 136 is applied to the approximate ninety degree corner where the flange 110 meets the EMI filter 128.

In this way, the braze joint 138 connecting the ceramic insulator 118 to the flange 110 is blocked and is thus not used as a conducting path for grounding of the EMI filter 128. Thus, the potential disadvantages of brittleness of the braze joint 138 or impurities in the braze material, among others, is avoided by creating a separate conducting path for grounding of the EMI filter 128. As seen in FIGS. 3A and 3B, a substantially larger cross-section of conducting material in the conducting adhesive 136 can be used to form the grounding connection as there is ample space at the abutment of the flange 110 and the EMI filter 128. An increase in the size of the surface area for grounding (as opposed to utilizing the gold braze) permits the use of larger EMI filters 128. While not seen in FIGS. 3A and 3B, the conducting adhesive 136 may be applied along the face of the flange 110 the full length of the EMI filters 128. Since the braze joint is insulated from contact with the EMI filter 128, the variability associated with the quality of the braze joint and the material making up the braze joint is avoided. Instead, a separate electric conducting pathway is utilized via the conductive adhesive.

FIG. 4A is a cross-sectional top view of the filtered feedthrough assembly 100 taken along the section line 4A shown in FIG. 2. FIG. 4B shows a close-up view of a feedthrough wire 104 exiting the EMI filter 128. As seen in FIGS. 4A and 4B, a non-conductive adhesive 140 is applied to the feedthrough wires 104 at the ports 134 of the insulating washer 132. And, an electrically conductive adhesive 142 is applied to the feedthrough wires 104 where the wires 104 are positioned in the ports 130 of the EMI filter 128. The non-conducting adhesive 140 applied to the wires 104 egressing the EMI filter 128 aid in strain-relieving the wires 104 and to protect the electrically conductive adhesive 142 in the EMI filter 128 against separation and/or damage if the wires 104 are bent and/or moved. Non-conductive adhesive 140 may also be dispensed on the gold braze 138 connecting the ceramic insulator 118 to the flange 110.

As seen in FIG. 4C, which is a close-up view a portion of the filtered feedthrough assembly 100 where the ceramic insulator 118 abuts the EMI filter 128 (with the double-sided insulating washer positioned there between), the ceramic insulator 118 includes counter bores 144 leading into the wire ports 120. The counter bores 144 typically contain gold brazing. In the brazing process, however, air pockets can be formed at the counter bores 144. To ensure the air does not expand and create voids and/or bubbles in the electrically conductive adhesive 142 adhered to the wires 104 in the EMI filter 128, non-conductive adhesive 140, such as insulating tape, is adhered to the counter bores 144.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A filtered feedthrough assembly for an implantable pulse generator, the filtered feedthrough assembly comprising:
    a flange that is electrically conductive and defines a feedthrough port through the flange, the feedthrough port extending from a can side face of the flange;
    an insulator disposed within the feedthrough port, the insulator secured to the flange at a joint defined between an outer perimeter surface of the insulator and an inner surface of the feedthrough port, the insulator configured to hold a plurality of feedthrough wires that extend through the insulator;
    a double-sided adhesive washer including a first side that is adhered to a face of the insulator and the can side face of the flange such that the double-sided adhesive washer extends across the joint, wherein the double-sided adhesive washer is electrically non-conductive;
    an EMI filter capacitor having a header side face that is adhered to a second side of the double-sided adhesive washer; and
    a conductive grounding connector extending from the EMI filter capacitor to the can side face of the flange, outside of the double-sided adhesive washer, to provide a grounding path between the EMI filter capacitor and the flange.

2. The filtered feedthrough assembly of claim 1, wherein the joint is a braze joint that includes an electrically conductive braze material applied between the insulator and the flange.

3. The filtered feedthrough assembly of claim 1, wherein the joint is one of a solder joint or a weld joint.

4. The filtered feedthrough assembly of claim 1, wherein the double-sided adhesive washer has a size and shape that substantially matches the header side face of the EMI filter capacitor.

5. The filtered feedthrough assembly of claim 1, wherein the double-sided adhesive washer has a rectangular shape.

6. The filtered feedthrough assembly of claim 1, wherein the double-sided adhesive washer defines a plurality of through-holes that are sized, shaped, and positioned to each receive a corresponding one of the feedthrough wires therethrough.

7. The filtered feedthrough assembly of claim 1, wherein the double-sided adhesive washer physically separates the EMI filter capacitor from the insulator and the flange.

8. The filtered feedthrough assembly of claim 1, wherein the conductive grounding connector is an electrically conductive adhesive.

9. The filtered feedthrough assembly of claim 1, wherein the conductive grounding connector is disposed on the can side face of the flange and contacts an edge of the EMI filter capacitor at an intersection between the header side face and an outer perimeter surface of the EMI filter capacitor.

10. The filtered feedthrough assembly of claim 9, wherein the conductive grounding connector extends along the edge of the EMI filter capacitor for a full length of the EMI filter capacitor.

11. The filtered feedthrough assembly of claim 1, wherein the insulator defines a plurality of wire ports configured to receive corresponding ones of the feedthrough wires, each of the wire ports includes a counter bore extending from the face of the insulator, wherein a non-conductive adhesive is disposed within each of the counter bores to secure the feedthrough wires to the insulator.

12. The filtered feedthrough assembly of claim 11, wherein the double-sided adhesive washer at least partially covers the non-conductive adhesive that is disposed within the counter bores.

13. The filtered feedthrough assembly of claim 1, further comprising a non-conductive adhesive applied directly on the joint, and the double-sided adhesive washer covers the non-conductive adhesive.

14. The filtered feedthrough assembly of claim 1, wherein a surface area of the double-sided adhesive washer along the first side thereof is greater than a surface area of the face of the insulator.

15. A method of manufacturing a filtered feedthrough assembly for use with an implantable pulse generator, the method comprising:
    securing an outer perimeter surface of an insulator to an inner surface of a feedthrough port of a flange at a joint such that the insulator is disposed within the feedthrough port, the insulator configured to hold a plurality of feedthrough wires that extend through the insulator;
    applying a double-sided adhesive washer to the flange and the insulator such that a first side of the double-sided adhesive washer adheres to a face of the insulator and a can side face of the flange and the double-sided adhesive washer extends across the joint, wherein the double-sided adhesive washer is electrically non-conductive and the flange is electrically conductive;
    attaching an EMI filter capacitor to a second side of the double-sided adhesive washer such that the second side adheres to a header side face of the EMI filter capacitor; and
    applying a conductive grounding connector that extends from the EMI filter capacitor to the can side face of the flange, outside of the double-sided adhesive washer, to provide a grounding path between the EMI filter capacitor and the flange.

16. The method of claim 15, wherein securing the outer perimeter surface of the insulator to the inner surface of the feedthrough port comprises brazing using an electrically conductive braze material to form the joint.

17. The method of claim 15, wherein the double-sided adhesive washer defines a plurality of through-holes that are sized, shaped, and applying the double-sided adhesive washer comprises loading the double-sided adhesive washer onto the feedthrough wires to reach the face of the insulator and the can side face of the flange.

18. The method of claim 15, further comprising applying a non-conductive adhesive directly on the joint between the insulator and the flange, and the double-sided adhesive washer covers the non-conductive adhesive as the double-sided adhesive washer is applied onto the face of the insulator and the can side face of the flange.

19. The method of claim 15, wherein the conductive grounding connector is an electrically conductive adhesive.

20. The method of claim 15, wherein the conductive grounding connector is applied to the can side face of the flange and an edge of the EMI filter capacitor at an intersection between the header side face and an outer perimeter surface of the EMI filter capacitor.

\* \* \* \* \*